United States Patent [19]

Tachi

[11] Patent Number: 4,775,887

[45] Date of Patent: Oct. 4, 1988

[54] OBSERVATION APPARATUS FOR ARTIFICIAL ORGANS

[75] Inventor: Hiroyuki Tachi, Tokyo, Japan

[73] Assignee: Aisin Seiki Kabushiki Kaisha, Kariya, Japan

[21] Appl. No.: 19,385

[22] Filed: Feb. 26, 1987

[30] Foreign Application Priority Data

Feb. 26, 1986 [JP] Japan .................................. 61-40797

[51] Int. Cl.⁴ .......................... H04N 7/18; A61B 1/04
[52] U.S. Cl. ....................................... 358/93; 358/98; 128/6; 128/903; 128/897; 623/3
[58] Field of Search ...................... 358/93, 98, 99, 100, 358/229; 128/6, 10; 623/3; 455/100, 129

[56] References Cited

U.S. PATENT DOCUMENTS

| | | | |
|---|---|---|---|
| 3,253,588 | 5/1966 | Vuilleumier et al. | .......... 455/100 X |
| 4,597,381 | 7/1986 | Oumi et al. | ........................ 358/98 X |
| 4,598,311 | 7/1986 | Bellina | ............................ 358/229 X |
| 4,633,304 | 12/1986 | Nagasaki | ............................... 358/98 |

Primary Examiner—Howard W. Britton
Assistant Examiner—Victor R. Kostak
Attorney, Agent, or Firm—Sughrue, Mion, Zinn, Macpeak & Seas

[57] ABSTRACT

An observation apparatus for an artificial organ such as an artificial heart includes a first casing having the artificial heart and a video signal generating and transmitting apparatus therein and a second casing independent and remote from the first casing having a video signal receiving and display apparatus therein.

2 Claims, 2 Drawing Sheets

OBSERVATION APPARATUS FOR ARTIFICIAL ORGANS

BACKGROUND OF THE INVENTION

1. Field of the Invention

The invention relates to observation apparatus for artificial organs, particularly for an artificial heart.

2. Description of the Prior Art

A conventional observation apparatus for artificial organs such as an artificial heart is described in Japanese application publication No. 60-106463.

Generally an artificial heart is attached to a human body. Therefore the body and artificial heart are covered with a sheet so that it is difficult to observe them.

In a conventional observation apparatus for artificial organs, as shown in FIG. 3, an artificial heart 20 is housed in a casing 23 and an image fiber 21 is attached to the casing 23. One end of the image fiber 21 is arranged so a to face toward the artificial heart 20, and the other end of the image fiber 21 is connected to a visual display like a video monitor (not shown) independent of the artificial heart.

Thus, a view of the artificial heart 20, which is transmitted through the image fiber 21 to the visual display, is displayed in the visual display. Therefore, even though the artificial heart 20 is covered by a sheet, it is possible to observe the artificial heart 20.

However, in a conventional observation apparatus the casing 23 and the visual display are connected with each other through an image fiber 21. Since the image fiber 21 is thick, bulky and easily broken, handling it is very troublesome. Further, as the image fiber 21 is very expensive, the total cost of the obseration apparatus increases.

Since the optical signal is easily reduced during transmission through the image fiber 21, it is required that the length of the image fiber 21 between the casing 23 and the visual display be as short as possible so as to clearly display the view of the artificial heart 20. However, if the visual display is arranged near the casing 23 for the artificial heart 20, the handling of the conventional observation apparatus is troublesome at this point.

SUMMARY OF THE INVENTION

The object of the invention is to provide an improved observation apparatus for artificial organs in which the above drawbacks have been obviated.

This object is realized by an observation apparatus for an artificial organ comprising a casing for housing the artificial organ therein, a view signal generating device mounted in the casing so as to take pictures of the artificial organ, a radio transmitter for the view signal mounted in the casing, a radio receiver for the view signal from the radio transmitter, and a visual display independent of the artificial organ for displaying the view of the artificial organ from the radio receiver.

The view of the artificial organ is transmitted to the visual display be radio so as to be displayed in the visual display. Therefore, there is no material link between the artificial organ and the visual display whereby it is possible to observe the artificial organ on the visual display in any convenient remote location.

The foregoing and other objects, features and advantages of the invention will be apparent from the following more particular description of a preferred embodiment of the invention as illustrated in the accompanying drawings.

DETAILED DESCRIPTION OF THE INVENTION

Figure 1:
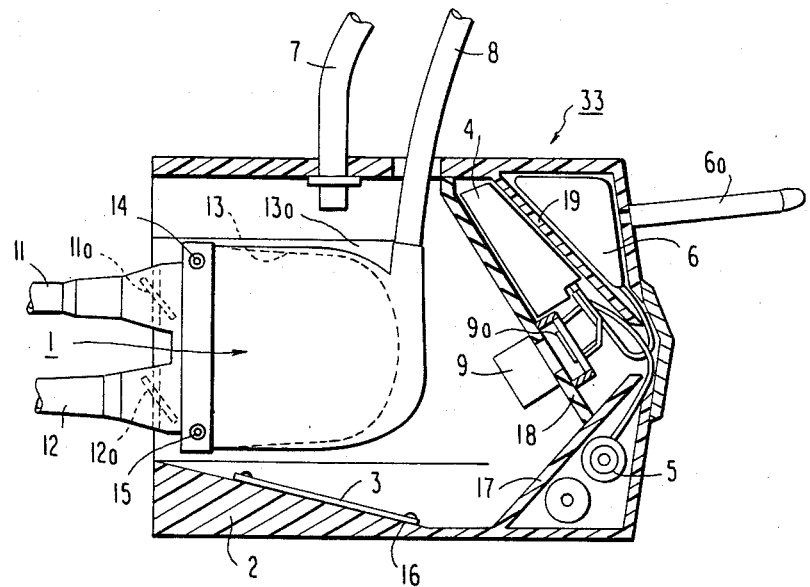
FIG. 1 is a sectional view showing an embodiment according to the present invention.
Figure 3:
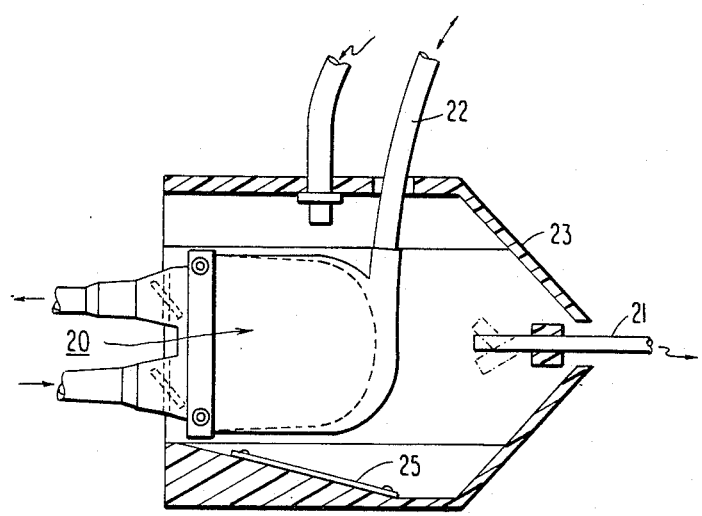
FIG. 3 is a sectional view showing a conventional apparatus.
Figure 2A:
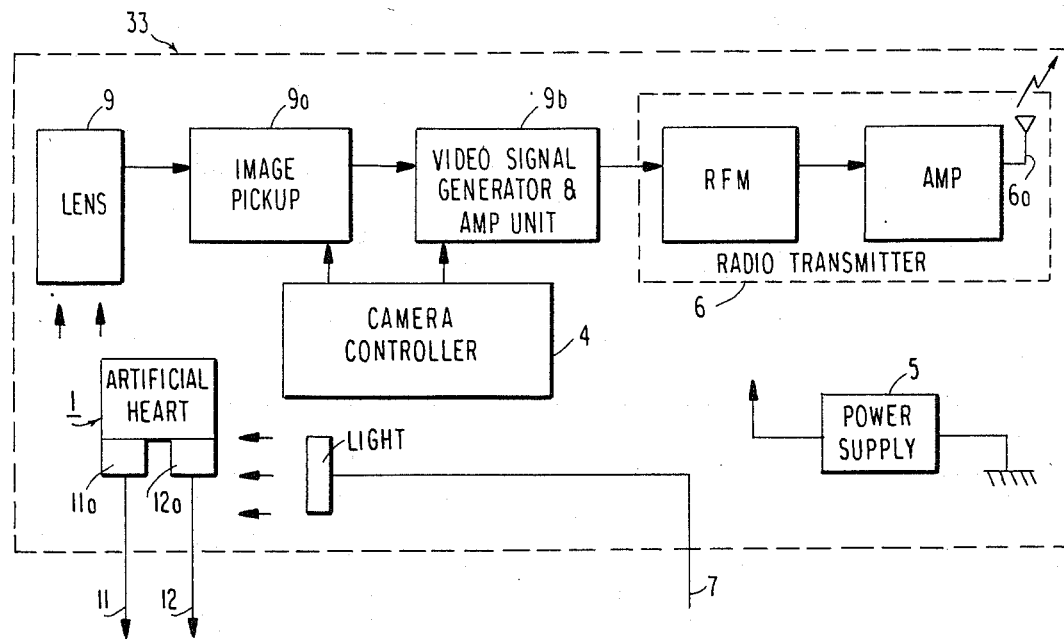
FIG. 2a is a block diagram showing the transmission apparatus.
Figure 2B:
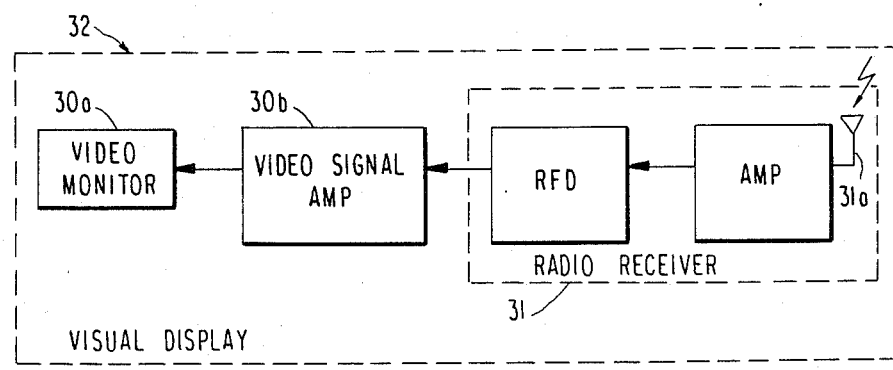
FIG. 2b is a block diagram of the receiving apparatus.

Referring to FIGS. 1 and 2, an artificial heart 1, which is adapted to be attached to a human body (not shown) is housed in a casing 2. The artificial heart 1 includes a pump case 13a and a compressible bag 13 housed in the pump case 13a. The pump case 13a is connected to a pressure source (not shown) through a tube 8. The compressible bag 13 is connected to a pair of tubes 11, 12, with one tube 11 for blood outflow and the other tube 12 for blood inflow. A first check valve 12a is disposed between the tube 12 and the compressible bag 13 so as to permit blood only to flow from the tube 12 to the compressible bag 13. A second check valve 11a is disposed between the tube 11 and the compressible bag 13 so a to permit blood only to flow from the compressible bag 13 to the tube 11.

Therefore, by supplying pressure from the pressure source into the pump case 13a through the tube 8, the compressible bag 13 deflates to pump blood in the compressible bag 13 out from the compressible bag 13 through the tube 11 to the human body. After that, by supplying vacuum from the pressure source into the pump case 13a through the tube 8, the compressible bag 13 inflates and blood flows through the tube 12 from the human body into the compressible bag 13. This inflate and deflate cycle is repeated so that blood circulates in the human body.

The pump case 13a is housed in a substantially cube-shaped casing 2 and secured to the casing 2 by bolts 14, 15. At the upper side of the casing 2 a light guide tube 7 enters the casing. This light guide tube 7 is connected to a light source (not shown) at one end of thereof and extended into the casing 2 at the other end. THerefore, the inner space of the casing 2 and the artificial heart 1 are illuminated. On the lower side of the casing 2 a reflector or mirror 3 is fixed so as to reflect the light from the artificial heart 1 to the right side of the casing 2.

In the right side of the casing 2, two partition plates 17, 19 are integrally formed with the casing 2. Further, a supporting plate 18 is arranged so as to face towards the first partition plate 19. This supporting plate 18 is connected to the upper side of the casing 2 and the second partition plate 17 at the upper end and the lower end thereof, respectively.

A lens 9 is mounted on the supporting plate 18 and this lens 9 is aligned with a CCD image pick up device 9a. The CCD image pick up device 9a is controlled by a camera controller 4 disposed between the supporting plate 18 and the first partition 19. The camera controller 4 also controls a video signal generating and amplifying unit 9b. Thereby, the view of the artificial heart 1 received by the lens 9 is changed into a video signal.

Further, a radio transmitter 6 is disposed between the first partition plate 19 and the casing 2 and an antenna 6a of the radio transmitter 6 is projected from the casing 2. The radio transmitter 6 includes a radio frequency modulator RFM and a high frequency amplifier AMP. Batteries 5 are disposed between the second partition plate 17 and the casing 2. The batteries 5 energize the CCD image pick up device 9a, the video signal generating and amplifying unit 9b, the camera controller 4 and the radio transmitter 6.

The observation apparatus for artificial organs 33 described above operates as follows:

As shown in FIG. 2a, the inner space of the casing 2 is illuminated by the light guide tube 7 and the view of the artificial heart 1 is reflected by the relector 3 to the CCD image pick up device 9a through the lens 9. The image on the CCD image pick up device 9a is changed from a light signal into an electrical signal. This electrical signal is read in turn by the camera controller 4 and processed into a video signal by the video signal generating and amplifying unit 9b. After high frequency modulation in the radio transmitter 6 the video signal is transmitted from the antenna 6a.

The transmitted video signal is received by an antenna 31a of a visual display 32, shown in FIG. 26, which is separated from the artificial heart housing and transmission apparatus 33 shown in FIG. 2a. The received video signal is amplified by an amplifier AMP and demodulated by a radio frequency demodulator RFD in a radio receiver 31. The original video signal is again generated and the video signal is supplied to a video monitor 30a of the visual display 32 through a video signal amplifier 30b so that the view of the artificial heart 1 is displayed on the video monitor 30a.

Therefore, even through the artificial heart 1 attached to the human body is covered by a sheet, it is possible to observe the operting state of the artificial heart 1 on the video monitor 30a since the view of the artificial heart 1 is transmitted to the visual display 32 by the radio transmitter 6. Since there exists no material link between the artificial heart 1 and the visual display 32 and since the visual display 32 is separated from the human body, the handling of the visual display 32 is very convenient.

While the invention has been particularly shown and described with reference to preferred embodiments thereof it will be understood by those in the art that the foregoing and other changes in form and details may be made therein without departing from the spirit and scope of the invention.

What is claimed is:

1. An observation apparatus for an artificial heart comprising:
    a casing having an artificial heart mounted herein,
    illuminating means mounted in said casing adjacent one side of said artificial heart for illuminating said artificial heart,
    reflecting means mounted in said casing on the opposite side of said artificial heart,
    lens means mounted in said casing at one end thereof,
    said lens means being focused on said reflecting means for forming an image of said artificial heart,
    electrical signal generating means including an image pickup means mounted in said casing and connected to said lens means for changing the image of said artificial heart into an electrical signal,
    video signal generating means mounted in said casing and connected to said signal generating means for processing said electrical signal into a video signal,
    radio transmitting means mounted in said casing and connected to said video signal generating means for transmitting said video signal externally of said casing,
    battery means mounted in said casing and connected to said signal generating means and said radio transmitting means for energization thereof,
    radio receiving means separate and independent from said casing for receiving said video signal from said radio transmitting means and
    visual display means connected to said radio receiving means for displaying the image of said artificial heart received by said radio receiving means.

2. An obseration apparatus as set forth in claim 1, further comprising a common housing in which said radio receiving means and said visual display means are mounted, said visual display means including a monitor for displaying the image of said artificial heart

* * * * *